United States Patent [19]

Cousse et al.

[11] Patent Number: 4,510,142
[45] Date of Patent: Apr. 9, 1985

[54] DERIVATIVES OF BIPHENYL ALKYL CARBOXYLATES AND THEIR USE AS MEDICAMENTS

[75] Inventors: Henry Cousse; Gilbert Mouzin; Jean-Pierre Tarayre; Jean-Pierre Rieu, all of Castres, France

[73] Assignee: Pierre Fabre S.A., Paris, France

[21] Appl. No.: 433,987

[22] Filed: Oct. 12, 1982

[30] Foreign Application Priority Data

Oct. 14, 1981 [FR] France .................. 81 19316

[51] Int. Cl.³ .................. A61K 31/44; A61K 31/495; C07D 341/04; C07D 213/75
[52] U.S. Cl. .................. 514/255; 514/330; 514/354; 514/534; 544/390; 544/391; 546/226; 546/309; 560/102
[58] Field of Search .................. 544/391, 390; 546/309, 546/342, 226; 560/102; 424/250, 263, 267, 308

[56] References Cited

U.S. PATENT DOCUMENTS

| | | | |
|---|---|---|---|
| 4,297,357 | 10/1981 | Miki et al. | 546/309 |
| 4,304,788 | 12/1981 | Edge et al. | 560/102 |
| 4,332,961 | 6/1982 | Takahashi et al. | 546/309 |
| 4,390,715 | 6/1983 | Holan et al. | 560/102 |

FOREIGN PATENT DOCUMENTS

| | | |
|---|---|---|
| 5737 | 1/1968 | France . |
| 6978 | 5/1969 | France . |
| 2185410 | 1/1974 | France . |

*Primary Examiner*—Glennon H. Hollrah
*Assistant Examiner*—James H. Turnipseed

*Attorney, Agent, or Firm*—Fleit, Jacobson, Cohn & Price

[57] ABSTRACT

This invention relates to new derivatives of biphenyl alkyl carboxylates, to a process for the preparation thereof and the use thereof as medicaments.

The new derivatives according to the present invention correspond to general formula (I):

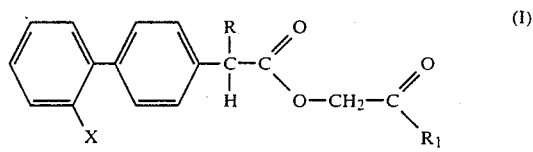

wherein

X represents a hydrogen atom or a halogen atom,

R represents a hydrogen atom or an alkyl group, and $R_1$ represents the following groups:

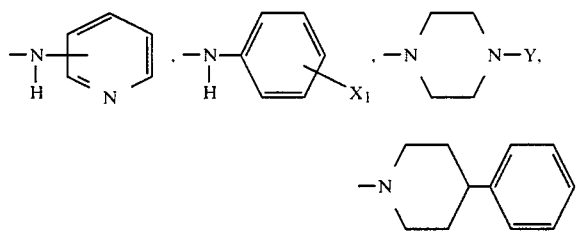

These compounds will notably be used in the treatment of obstinate pains and inflammatory syndromes.

12 Claims, No Drawings

DERIVATIVES OF BIPHENYL ALKYL CARBOXYLATES AND THEIR USE AS MEDICAMENTS

BACKGROUND OF THE INVENTION

This invention relates to new derivatives of biphenyl acetic acid, a process for the preparation thereof and the use thereof in therapeutics.

These new active principles have anti-inflammatory and pain-killing properties and are notably useful as medicaments for the treatment of various pains and types of rheumatism.

The invention also relates to pharmaceutical compositions containing these new compounds and the therapeutically acceptable salts thereof.

SUMMARY OF THE INVENTION

The compounds which are an object of the present invention correspond to the general formula (I):

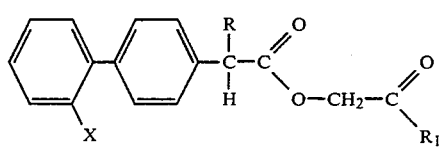

wherein

X represents a hydrogen atom or a halogen atom,
R represents a hydrogen atom or an alkyl group, and
$R_1$ represents the following groups:

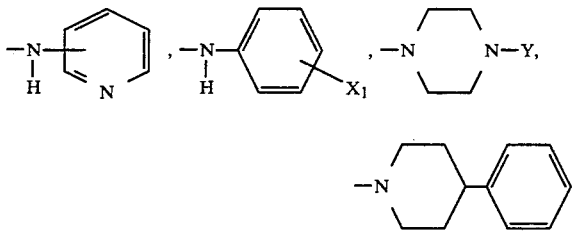

wherein $X_1$ represents a hydrogen atom or a halogen atom or a $CF_3$ radical, and Y represents an alkyl group or an aryl group optionally substituted by a halogen atom or by a $CF_3$ radical.

DETAILED DESCRIPTION

The term "alkyl" as used herein designates a linear or branched hydrocarbon radical containing from 1 to 4 carbon atoms.

The therapeutically acceptable salts of the compounds corresponding to the general formula (I) are mainly addition salts or salts of mineral or organic acids, such as hydrochloric acid, phosphoric acid, sulphuric acid, maleic acid, succinic acid, fumaric acid and citric acid etc.

The new derivatives of biphenyl acetic acid corresponding to the general formula (I) according to the present invention may be obtained, for example, by treating an acid corresponding to general formula (II):

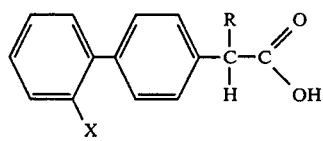

with a chloroacetylated derivative corresponding to general formula (III):

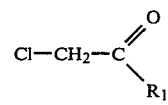

in the presence of an alkaline carbonate and a catalyst, such as potassium iodide.

Some non-limiting Examples of the preparation of derivatives corresponding to the general formula (I) according to the present invention will be provided in the following simply by way of illustration.

EXAMPLE 1

Preparation of N-phenyl parabiphenylacetoxyacetamide 11 grammes (80 mmoles) of potassium carbonate are ground in the presence of 300 mg of potassium iodide. This mixture is added to 16.34 g (77 mmoles) of p-biphenylacetic acid in suspension in a solution of 11.9 g (70 mmoles) of chloroacetanilide in 200 ml of methylethylketone.

The reaction mixture is brought to reflux for 5 hours. After returning to ambient temperature, the mixture is poured into cold water. The organic phase is washed with an aqueous solution of sodium carbonate, then with water until neutral. It is dried over sodium sulphate in the presence of animal charcoal, and the insoluble matter is then removed by filtration. The solvent is evaporated under reduced pressure. The resulting crystals are recrystallised in a methylethylketone-hexane mixture (30/70). 73% of product corresponding to the following formula are recovered after filtration and drying:

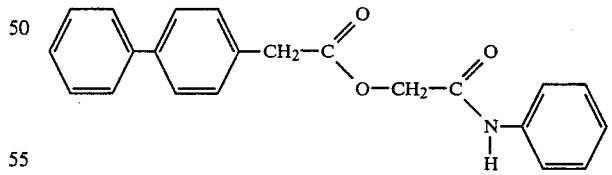

Empirical formula: $C_{22}H_{19}NO_3$
Molecular weight: 345.4
Crystals: white
Melting point: 133° C.
Plate chromatography: support: silica gel 60 F. 254 Merck ®, solvent: ethyl acetate-petroleum ether 30/70, detection: UV and iodine, Rf: 0.35.

Infrared spectrum (KBr pellet): $\nu C=O$ (ester) 1750 cm$^{-1}$; $\nu C=O$ (amide) 1660 cm$^{-1}$.

NMR spectrum (DMSO d$_6$): δppm: 3.85 (s, 2H, CH$_2$—COO); 4.75 (s, 2H, $$CO_2-CH_2-\overset{\overset{O}{\|}}{C}-N);$$

7–7.8 (m, 14H aromatic); 10.05 (s, 1H,N—H)

EXAMPLE 2

Preparation of N(metatrifluoromethylphenyl)parabiphenylacetoxyacetamide

55% of product corresponding to the following formula are obtained by a method similar to the one described in Example 1, but using metatrifluoromethyl chloroacetanilide:

Empirical formula: $C_{23}H_{18}F_3NO_3$
Molecular weight: 413.4
Crystals: white
Melting point: 90° C.

Plate chromatography: support: silica gel 60 F. 254 Merck ®, solvent: ethyl acetate-petroleum ether 30/70, detection: UV and iodine, Rf: 0.35.

Infrared spectrum (KBr): $\nu C=O$ (ester) 1740 cm$^{-1}$; $\nu C=O$ (amide) 1670 cm$^{-1}$.

NMR spectrum (DMSO d$_6$): δppm: 3.9 (s, 2H, $\underline{CH_2}$—CO$_2$); 4.75 (s, 2H, $$CO_2-CH_2-\overset{\overset{O}{\|}}{C}-N);$$

7.2–7.8 (m, 13H aromatic); 10.4 (s, 1H, NH).

EXAMPLE 3

Preparation of 4-methyl-1-parabiphenylacetoxyacetyl piperazine hydrochloride

60% of product corresponding to the following formula are obtained by a method similar to the one described in Example 1, but using 4-methyl-1-chloroacetyl piperazine:

Empirical formula: $C_{21}H_{25}ClN_2O_3$
Molecular weight: 388.9
Crystals: white
Melting point: 174°–176° C.

Plate chromatography: support: silica gel 60 F. 254 Merck ®, solvent: chloroform-methanol 90/10, detection: UV and iodine, Rf: 0.5.

Infrared spectrum (KBr): $\nu C=O$ (ester) 1745 cm$^{-1}$; $\nu C=O$ (amide) 1670 cm$^{-1}$.

EXAMPLE 4

Preparation of 4-phenyl-1-parabiphenylacetoxyacetyl piperidine

65% of product corresponding to the following formula are obtained by a method similar to the one described in Example 1, but using 4-phenyl-1-chloroacetyl piperidine:

Empirical formula: $C_{27}H_{27}NO_3$
Molecular weight: 413.5
Crystals: white
Melting point: 93° C.

Plate chromatography: support: silica gel 60 F. 254 Merck ®, solvent: ethyl acetate-petroleum ether 50/50, detection: UV and iodine, Rf: 0.45.

Infrared spectrum (KBr): $\nu C=O$ (ester) 1750 cm$^{-1}$; $\nu C=O$ (amide) 1660 cm$^{-1}$.

EXAMPLE 5

Preparation of 4-(metatrifluoromethylphenyl)-1-parabiphenylacetoxyacetyl piperazine hydrochloride 70% of product corresponding to the following formula are obtained by a method similar to the one described in Example 1, but using 4-(metatrifluoromethylphenyl)-1-chloroacetyl piperazine and hydrochloric acid as a salt-forming agent:

Empirical formula: $C_{27}H_{26}ClF_3N_2O_3$
Molecular weight: 518.9
Crystals: white
Melting point: slow decomposition between 100° and 110° C.

Plate chromatography: support: silica gel 60 F. 254 Merck ®, solvent: ethyl acetate-petroleum ether, detection: UV and iodine, Rf: 0.40.

Infrared spectrum (KBr): $\nu$C=O (ester) 1750 cm$^{-1}$ and 84 C=O (amide) 1670 cm$^{-1}$.

EXAMPLE 6

Preparation of 4-phenyl-1-[(4-phenyl phenyl)acetoxyacetyl] piperazine:

71% of product corresponding to the following formula are obtained by a method similar to the one described in Example 1, but using 4-phenyl-1-chloroacetyl piperazine:

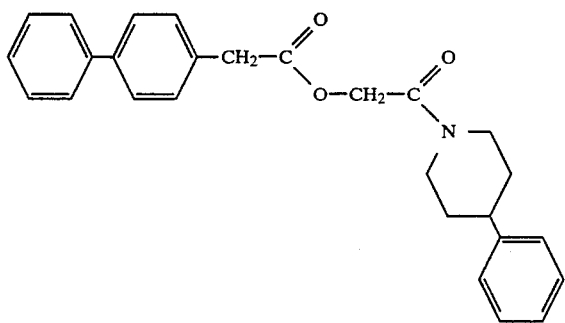

Empirical formula: $C_{26}H_{26}N_2O_3$
Molecular weight: 414.5
Crystals: white
Melting point: 92° C.

Plate chromatography: support: silica gel 60 F. 254 Merck ®, solvent: ethyl acetate-petroleum ether 30/70, detection: UV and iodine, Rf: 0.65.

Infrared spectrum (KBr): $\nu$C=O (ester) 1740 cm$^{-1}$ and $\nu$C=O (amide) 1650 cm$^{-1}$.

NMR spectrum (DMSO d$_6$): δppm: 2.9–3.2 (m, 4H, Ph—N—CH$_2$); 3.2–3.7 (m, 4H,

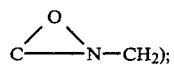

3.8 (s, 2H, Ph—CH$_2$—CO); 4.7 (s, 2H, O—CH$_2$—C=O); 6.8–7.7 (m, 14H aromatic).

EXAMPLE 7

Preparation of 4-methyl-1-[(4-orthochlorophenyl phenyl) acetoxyacetyl] piperazine hydrochloride 83% of product corresponding to the following formula are obtained by a method similar to the one described in Example 1, but using orthochlorobiphenyl acetic acid and chloroacetyl piperazine, then forming a salt with hydrochloric acid:

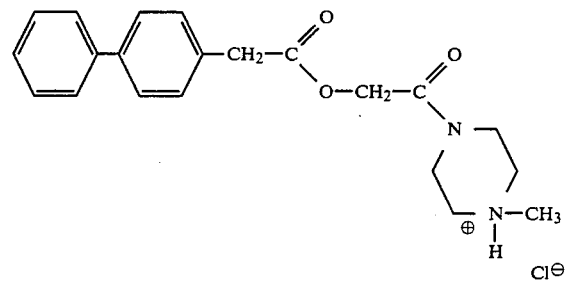

Empirical formula: $C_{21}H_{24}Cl_2N_2O_3$
Molecular weight: 423.3
Crystals: white
Melting point: slow decomposition from 190° to 200° C.

Plate chromatography: support: silica gel 60 F. 254 Merck ®, solvent: chloroform-methanol 90/10, detection: UV and iodine,
Rf: 0.55.

Infrared spectrum (KBr): $\nu$C=O (ester) 1750 cm$^{-1}$ and $\nu$C=O (amide) 1670 cm$^{-1}$.

EXAMPLE 8

4-phenyl-1-[(4-orthochlorophenyl)phenyl-acetoxyacetyl] piperazine hydrochloride

67% of product corresponding to the following formula are obtained by a method similar to the one described in Example 1, but using orthochlorobiphenyl acetic acid, and 4-phenyl chloroacetyl piperazine, then forming a salt with hydrochloric acid:

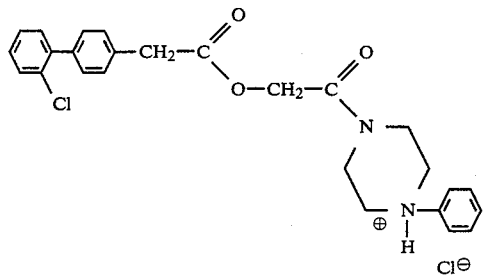

Empirical formula: $C_{26}H_{26}Cl_2N_2O_3$
Molecular weight: 485.4
Crystals: white
Melting point: 136°–140° C.

Plate chromatography: support: silica gel 60 F. 254 Merck ®, solvent: chloroform-methanol 95/5, detection: UV and iodine, RF: 0.55.

Infrared spectrum (KBr): $\nu$C=O (ester) 1750 cm$^{-1}$ and $\nu$C=O (amide) 1670 cm$^{-1}$.

EXAMPLE 9

Preparation of 4-metatrifluoromethylphenyl-1-[4-(orthochlorophenyl)phenyl acetoxyacetyl] piperazine hydrochloride 62% of product corresponding to the following formula are obtained by a method similar to the one described in Example 1, but using orthochlorobiphenyl acetic acid and 4-phenyl chloroacetyl piperazine, then forming a salt with hydrochloric acid:

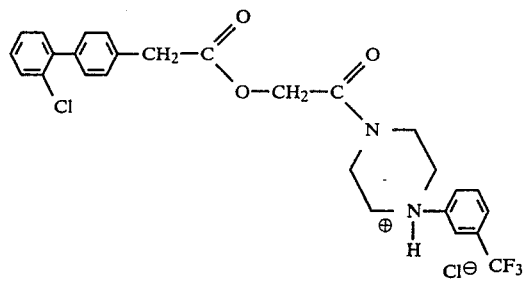

Empirical formula: $C_{27}H_{25}Cl_2N_2O_3F_3$
Molecular weight: 553.4
Crystals: white
Melting point: 134° C.
Plate chromatography: support: silica gel 60 F. 254 Merck ®, solvent: chloroform-methanol 95/5, detection: UV and iodine, Rf: 0.61.
Infrared spectrum (KBr): $\nu C=O$ (ester) 1755 cm$^{-1}$ and $\nu C=O$ (amide) 1670 cm$^{-1}$.

EXAMPLE 10

Preparation of 4-(metachlorophenyl)-1-[(4-orthochlorophenyl phenyl)acetoxyacetyl] piperazine hydrochloride 73% of product corresponding to the following formula are obtained by a method similar to the one described in Example 1, but using orthochlorobiphenyl acetic acid and 1-chloroacetyl-4-metachlorophenyl piperazine, then forming a salt with hydrochloric acid:

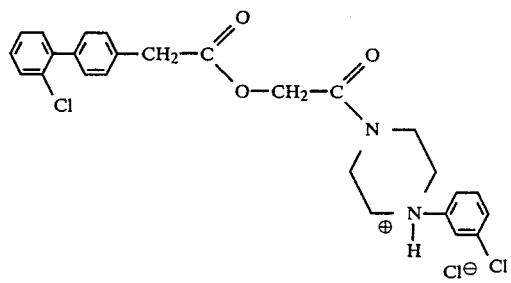

Empirical formula: $C_{26}H_{25}Cl_3N_2O_3$
Molecular weight: 519.8
Crystals: white
Melting point: 128° C.
Plate chromatography: support: silica gel 60 F. 254 Merck ®, solvent: chloroform-metahnol 95/5, detection: UV and iodine, Rf: 0.60.
Infrared spectrum (KBr): $\nu C=O$ (ester) 1750 cm$^{-1}$ and $\nu C=O$ (amide) 1660 cm$^{-1}$.

EXAMPLE 11

Preparation of [2-(4-phenyl 1-piperazinyl)-2-oxo] ethyl 2-parabiphenyl propionate 50% of product corresponding to the following formula are obtained by a method similar to the one described in Example 1, but using 2-para-biphenylyl proprionic acid and N'-phenyl-N-chloroacetyl piperazine:

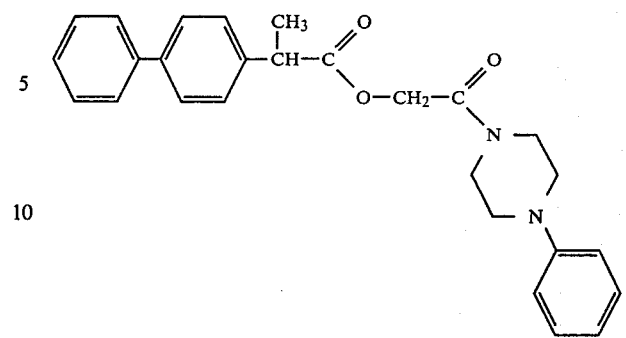

Empirical formula: $C_{27}H_{28}N_2O_2$
Molecular weight: 428.5
Crystals: white
Melting point: 92° C.
Plate chromatography: support: silica gel 60 F. 254 Merck ®, solvent: toluene/ethyl acetate 70/30, detection: UV and iodine, Rf: 0.38.
Infrared spectrum (KBr): $\nu C=O$ (ester) 1740 cm$^{-1}$ and $\nu C=O$ (amide) 1660 cm$^{-1}$.

EXAMPLE 12

Preparation of 2-(4-methylpiperazino)-2-oxoethyl 2-(2'-chloro-4-biphenylyl)propionate hydrochloride 62% of product corresponding to the following formula are obtained by a method similar to the one described in Example 1, but using 2-(4-orthochlorophenyl phenyl) propionic acid and 4-methyl-1-chloroacetyl piperazine, then forming a salt with hydrochloric acid:

Empirical formula: $C_{22}H_{26}Cl_2N_2O_3$
Molecular weight: 437.3
Crystals: white
Melting point: 210° C. (instantaneous)
Plate chromatography: support: silica gel 60 F. 254 Merck ®, solvent: chloroform-methanol 90/10, detection: UV and iodine, Rf: 0.51.
Infrared spectrum (KBr): $\nu C=O$ (ester) 1745 cm$^{-1}$ and $\nu C=O$ (amide) 1675 cm$^{-1}$.
NMR spectrum (DMSO d$_6$): $\delta$ppm: 1.45 (d, 3H,CH$_3$—C); 2.7 (s, 3H,CH$_3$—N); 2.8-4.2 (m, 10H, (CH$_2$)$_4$, exchangeable, CH—CH$_3$); 4.85 (s, 2H, O—CH$_2$—CO); 7.35 (s,8H aromatic).

EXAMPLE 13

Preparation of 2-(4-phenylpiperazino)-2-oxoethyl 2-(2'-chloro-4-biphenylyl)propionate 82% of product corresponding to the following formula are obtained by a method similar to the one described in Example 1, but using 2-(4-orthochlorophenyl phenyl)propionic acid and 1-phenyl chloroacetyl piperazine:

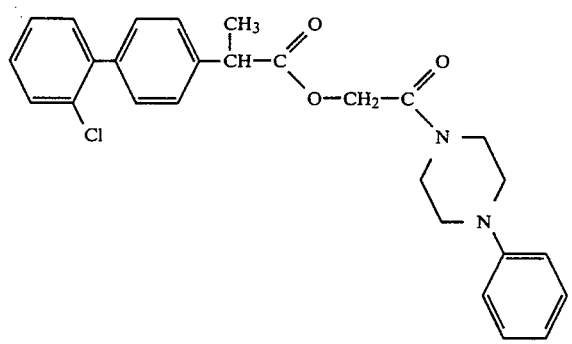

Empirical formula: $C_{27}H_{27}ClN_2O_3$
Molecular weight: 462.9
Crystals: light beige
Melting point: 114° C.
Plate chromatography: support: silica gel 60 G 254 Merck®, solvent: chloroform-methanol 99/1, detection: UV and iodine, Rf: 0.51.
Infrared spectrum (KBr): $\nu C=O$ (ester) 1745 cm$^{-1}$ and $\nu C=O$ (amide) 1650 cm$^{-1}$.
NMR spectrum (DMSO d$_6$): δppm: 2.95 (d,3H,$\underline{CH_3}$—C); 2.8–3.6 (m,8H,CH$_2$ piperazine); 3.6–4.2 (q,1H,$\underline{CH_3}$—$\underline{CH}$); 4.8 (s,2H, O—$\underline{CH_2}$—C=O); 6.6–7.5 (m,13H aromatic).

EXAMPLE 14

Preparation of 2-(4-phenylpiperidino)-2-oxoethyl 2-(2'-chloro-4-biphenylyl)propionate 75% of product corresponding to the following formula are obtained by a method similar to the one described in Example 1, but using 2-(4-orthochlorophenyl phenyl)propionic acid and 4-phenyl-1-chloroacetyl piperidine:

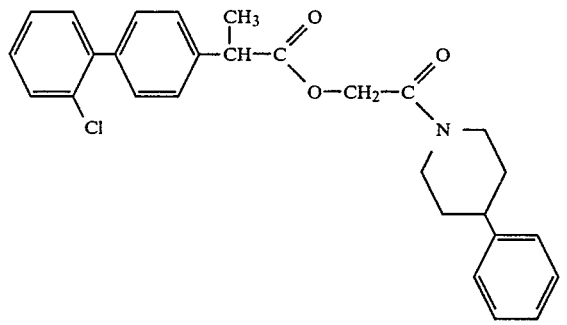

Empirical formula: $C_{28}H_{28}ClNO_3$
Molecular weight: 461.9
Crystals: white
Melting point: 74° C.
Plate chromatography: support: silica gel 60 F 254 Merck®, solvent: chloroform-methanol 99/1, detection: UV and iodine, Rf: 0.35.
Infrared spectrum (KBr): $\nu C=O$ (ester) 1740 cm$^{-1}$ and $\nu C=O$ (amide) 1650 cm$^{-1}$.

EXAMPLE 15

Preparation of 2-(2-aminopyridine)-2-oxoethyl 2-(2'-chloro-4-biphenylyl)propionate oxalate A product corresponding to the following formula is obtained by a method similar to the one described in Example 1, but using 2-(4-orthochlorophenyl phenyl)-propionic acid and 2-chloroacetylamino pyridine:

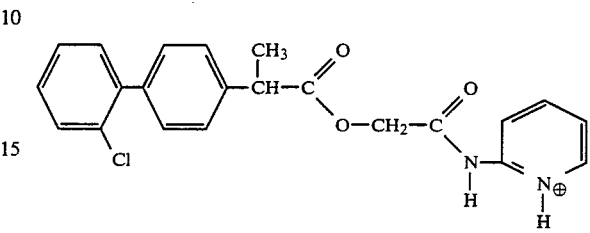

Empirical formula: $C_{24}H_{21}ClN_2O_7$
Molecular weight: 484.89
Crystals: light beige
Melting point: instantaneous 160° C.
Plate chromatography: support: silica gel 60 F 254 Merck®, solvent: chloroform-acetone 90/10, detection: UV and iodine, Rf: 0.81
Infrared spectrum (KBr): $\nu C=O$ (ester) 1735 cm$^{-1}$ and $\nu C=O$ (amide) 1630 cm$^{-1}$.

EXPERIMENTS

The above-described derivatives were the subject of pharmacological and toxicological experiments which have made it possible to demonstrate advantageous pain-killing and anti-inflammatory properties.

(A) Toxicology

A toxicity study was carried out on conventional mice weighing about 20 grams.
The compounds corresponding to the general formula I according to the present invention and the pharmaceutically acceptable salts thereof were administered orally. The DL$_{50}$ was calculated according to the method by L. C. Miller and M. L. Tainter—Proc. Soc. Exper. Biol. Med., 1944, 57,261. All of the administered compounds showed a very low toxicity and it will be particularly noted that the compounds of Examples 12 and 14 have a LD$_{50}$ greater than 500 mg/kg.

(B) Pharmacology

The pain-killing activity was studied according to Siegmund—J. Pharm. Exptl. ther., 1957, 119,453.
The compounds according to the present invention were administered orally 30 minutes before the injection of phenyl benzoquinone.
All of the administered compounds have an excellent pain-killing activity. In particular, the compounds of Examples 12 and 14 have a DE$_{50}$ respectively equal to 7 mg/kg and 5 mg/kg.
The anti-inflammatory properties were revealed in an oedema test by injecting carragenine into a rat's foot according to the technique of C. Winter, E. Ribley and G. Nuss—Proc. Soc. Exper. Biol. Med., 1962, 111, 544 547.
The products were administered orally in suspension in a Tween-water mixture 2 hours before the experiment. All the administered compounds have a good anti-inflammatory activity. It will particularly be noted that the compound of Example 14 has a DE$_{50}$ of 3 mg/kg.

For comparison purposes, the following Table shows the LD$_{50}$ and DE$_{50}$ values which were combined with some of the best known anti-inflammatory products.

| Products | LD$_{50}$ mg/kg p.o. | DE$_{50}$ (carragenine) mg/kg p.o. |
|---|---|---|
| Naproxen | 400 | 5 |
| Ibuprofen | 900 | 14 |
| Aspirin | 1500 | 135 |
| Phenylbutanone | 400 | 30 |
| Indometacine | 20 | 4 |

(C) Therapeutic uses

Bearing in mind the perfect tolerance of the compounds according to the present invention, and their pharmacological properties, they may be used in human or animal therapeutics in the treatment of obstinate pains of an inflammatory nature for which prolonged treatment is applicable.

The clinical results have proved to be satisfactory in cases of inflammatory or degenerative rheumatism.

The pharmaceutical preparations containing these active principles may be administered orally, parenterally or rectally. The quantity in a doseage unit is generally from 25 to 150 mg. These pharmaceutical compositions may also contain other pharmaceutically and therapeutically acceptable active principles.

Some examples of pharmaceutical preparations containing the active principles used in the experiments are provided in the following in an illustrative, non-limiting manner.

(a) Tablets
2-(4-methylpiperazino-2-oxoethyl 2-(2'-chloro-4-biphenylyl)propionate hydrochloride: 50 mg
excipient: lactose
(b) Capsules
2-(4-phenylpiperidino)-2-oxoethyl 2-(2'-chloro-4-biphenyl)propionate: 25 mg
(c) Adult suppositories
2-(4-phenylpiperidino)-2-oxoethyl 2-(2'-chloro-4-biphenylyl)propionate: 50 mg
Meprobamate: 100 mg
Semi-synthetic glycerides, quantity sufficient for 1 suppository of 1 g
(d) Injectable solution
2-(4-methylpiperazino)-2-oxoethyl 2-(2'-chloro-4-biphenylyl)propionate hydrochloride: 10 mg
Water for injectable preparation: 2 ml.

We claim:

1. A compound having the formula (I)

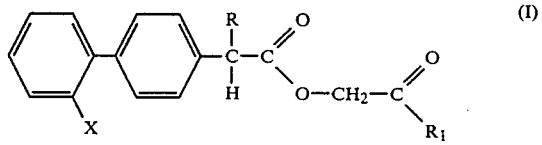

wherein x represents a monovalent group selected from a hydrogen atom and a halogen atom, R represents a monovalent group selected from a hydrogen atom or a straight or branched alkyl group having 1 to 4 carbon atoms, and R$_1$ represents a group selected from the following:

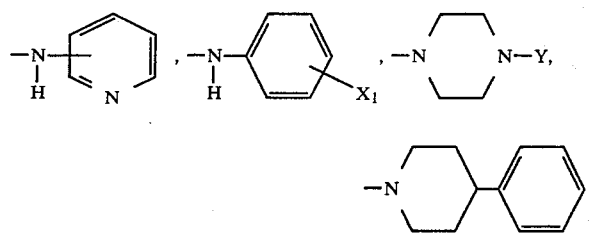

wherein X$_1$ represents a monovalent group selected from a hydrogen atom, a halogen atom and a CF$_3$ radical, and Y represents a monovalent group selected from a straight or branched alkyl group having 1 to 4 carbon atoms, a phenyl group and such group substituted by a substituent selected from a halogen atom and a CF$_3$ radical, and the therapeutically acceptable salts thereof.

2. Compounds corresponding to formula (I) of claim 1, and selected from the group consisting of:
N-phenyl parabiphenylacetoxyacetamide;
N(metatrifluoromethylphenyl)parabiphenylacetoxyacetamide;
4-methyl-1-parabiphenylacetoxyacetyl piperazine hydrochloride;
4-phenyl-1-parabiphenylacetoxyacetyl piperidine;
4-(metatrifluoromethylphenyl)-1-parabiphenylacetoxyacetyl piperazine hydrochloride;
4-phenyl-1-[(4-phenyl phenyl)acetoxyacetyl]piperazine;
4-methyl-1-[(4-orthochlorophenyl phenyl)acetoxyacetyl]piperazine hydrochloride;
4-phenyl-1-[4-(orthochlorophenyl)phenylacetoxyacetyl]piperazine hydrochloride;
4-(metatrifluoromethylphenyl-1-[4-(orthochlorophenyl)phenylacetoxyacetyl]piperazine hydrochloride;
4-(methachlorophenyl)-1-[(4-orthochlorophenyl phenyl)acetoxyacetyl]piperazine hydrochloride;
[2-(4-phenyl 1-piperazinyl)-2-oxo]ethyl 2-para biphenyl propionate;
2-(4-methylpiperazino)-2-oxoethyl 2-(2'-chloro-4-biphenylyl)propionate hydrochloride;
2-(4-phenylpiperazino)-2-oxoethyl 2-(2'-chloro-4-biphenylyl)propionate;
2-(4-phenylpiperidino)-2-oxoethyl 2-(2'-chloro-4-biphenylyl)propionate; and
2-(2-aminopyridine(-2-oxoethyl 2-(2'-chloro-4-biphenylyl)propionate oxalate.

3. The compound of claim 1 wherein R$_1$ is

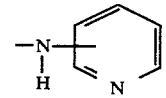

4. The compound of claim 1 wherein R$_1$ is

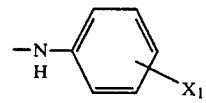

5. The compound of claim 1 wherein R$_1$ is

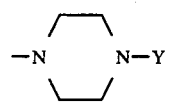

6. The compound of claim 1 wherein $R_1$ is

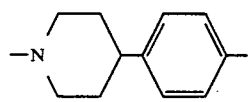

7. A compound according to claim 1 which is 2-(4-methylpiperazino)-2-oxoethyl 2-(2'-chloro-4-biphenylyl)propionate hydrochloride.

8. A compound according to claim 1 which is 2-(4-methylpiperazino)-2-oxoethyl 2-(2'-chloro-4-biphenylyl)propionate.

9. A compound according to claim 1 which is 2-(4-phenylpiperidino)-2-oxoethyl 2-(2'-chloro-4-biphenylyl)propionate.

10. A compound according to claim 1 which is 2-(4-phenylpiperidino)-2-oxoethyl2-(2'-chloro-4-biphenylyl)propionate hydrochloride.

11. A method for treatment of obstinate pains and painful inflammatory syndromes, in a subject selected from the group consisting of humans and animals, which comprises administration to said subject of an effective amount of a compound having the formula (I)

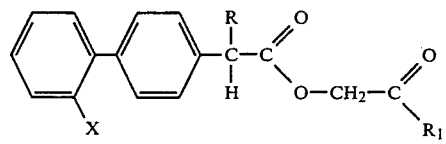

wherein X represents a monovalent group selected from a hydrogen atom and a halogen atom, R represents a monovalent group selected from a hydrogen atom or a straight or branched alkyl group having 1 to 4 carbon atoms, and $R_1$ represents a group selected from the following:

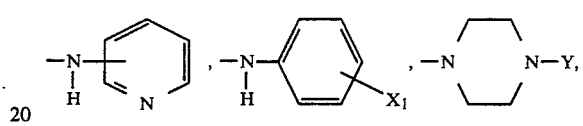

wherein $X_1$ represents a monovalent group selected from a hydrogen atom, a halogen atom and a $CF_3$ radical, and Y represents a monovalent group selected from a straight or branched alkyl group having 1 to 4 carbon atoms, a phenyl group and such group substituted by a substituent selected from a halogen atom and a $CF_3$ radical, and the therapeutically acceptable salts thereof.

12. Pharmaceutical compositions containing, in an amount effective to relieve obstinate pains and painful inflammatory syndromes, a compound corresponding to formula (I) of claim 1 as an active principle and a pharmaceutically acceptable carrier.

* * * * *